(12) United States Patent
Obermeier

(10) Patent No.: US 6,216,096 B1
(45) Date of Patent: Apr. 10, 2001

(54) ANALYSIS SYSTEM WITH TIME STANDARD

(75) Inventor: Wolfgang Obermeier, Heidelberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/127,074

(22) Filed: Jul. 31, 1998

(30) Foreign Application Priority Data

Aug. 2, 1997 (DE) .............................................. 197 33 445

(51) Int. Cl.⁷ ..................................................... G06F 15/00
(52) U.S. Cl. .......................... 702/177; 702/178; 702/187; 702/177; 702/176; 705/418
(58) Field of Search ..................................... 702/177, 178, 702/187, 176; 705/413, 418; 204/406, 412; 356/446, 226

(56) References Cited

U.S. PATENT DOCUMENTS 5,047,044 * 9/1991 Smith et al. ........................... 606/182
5,321,492 * 6/1994 Detwiler et al. ........................ 356/73

* cited by examiner

*Primary Examiner*—Kamini Shah
(74) *Attorney, Agent, or Firm*—Arent Fox Kintner Plotkin & Kahn, PLLC

(57) ABSTRACT

The invention relates to an analysis system having a time counter and a data processing unit (DPU) having a time standard. The test results produced by the analysis system along with the associated time values of the time counter are transferred to the DPU and processed therein. The associated time values of the time counter are then compared with the time values of the time standard to determine the absolute time values of the associated time values.

21 Claims, 2 Drawing Sheets

ANALYSIS SYSTEM WITH TIME STANDARD

FIELD OF THE INVENTION

The present invention relates generally to an analysis system having an analyzer with a time counter and a data processing unit (DPU) that contains a time standard. Test results from the analyzer, together with the time values from the time counter, are transferred to the DPU. The DPU then compares the time values from the time counter with the time values from the time standard to determine absolute time values.

BACKGROUND OF THE INVENTION

A number of portable analyzers are known in the prior art to carry out measurements. For example, analyzers that measure blood sugar levels by analyzing a blood sample that is applied to a testing element have become especially widespread. As a rule, such analyzers have a memory wherein test results and information such as the time of analysis are stored. For example, such an analyzer is described in the German patent document 4 328 630. The prior art further includes analysis systems that transmit test results from a test instrument to an evaluating unit. Such implements are becoming increasingly important in the care and education of diabetics. Based on individual tests, the diabetic can only determine whether to inject insulin. However, by recording blood sugar measurements over the day or for several days or weeks, the diabetic may gain information on how food intake, sports or other time dependent factors affect his blood sugar level. Moreover, by monitoring the time-function of the blood sugar level, the diabetic gains important information concerning how his particular body responds to the administration of insulin. The diabetic's data management system Camit® made by Boehringer Mannheim GmbH is already on the market. In this system, the data secured using a commercial blood sugar test instrument is transferred to a PC that shows the blood sugar level as a function of time and makes it possible to give the patient information concerning the effect of the above influences. Systems that record the blood sugar level over time are designed in such manner that the user initially carries out a number of measurements and then later transfers the test results to an evaluation unit. Such a design entails storing the times of testing together with the test results. Since such systems are required to operate reliably for months or years, the analyzer must include a highly accurate clock or allow the clock to be adjusted. Unfortunately, clocks that remain highly accurate at varying ambient temperatures are still comparatively expensive. Likewise, clock adjustment is an inconvenience for the user and requires additional operational elements which must be integrated into the analyzer. These additional elements make the analyzer more expensive. It is also undesireable in a lot of cases for the user to be able to change the time and manipulate the record. For example, recording the times at which a diabetic checked their blood sugar levels allows a physician to ascertain whether or not the diabetic is observing the physician's prescribed regimen. Another factor that may limit the effectiveness of such an analysis system is the time change that occurs between summer and winter and different time zones. For example, if the clock is adjusted to the local time when a user changes times zones, it may be unclear later exactly when the test data was entered. In such cases, it may be advantageous to block the option to adjust the analyzer's or time-counter's clock. Therefore, it is an object of the present invention to provide an analytical system that assigns times to the test results as accurately as possible without the use of expensive precision clocks or clock adjusting operational elements.

SUMMARY OF THE INVENTION

The above discussed objectives of the invention are attained using an analytical system as discussed below. The analyzer is provided with means to carry out testing to generate test results. An integrated time counter generates relative time values. A memory stores data records of the test results and their relative time values. A transmitting device transfers the stored data records to a DPU. A receiving device in the DPU receives the data records and the DPU processes the data records. The DPU contains a time standard. A calculating unit converts the relative time values into absolute time values by comparing the analyzer time values with the DPU's time standard time values.

The present invention uses an analyzer having a time counter that only needs to meet modest accuracy requirements. The analyzer is designed to store data records, test results and time values. The analyzer communicates with a DPU having a time-standard. By comparing the relative time values of the time counter with the time values from the time standard, the time counter time values can be converted into absolute time values. Thus, absolute time values can be assigned to the test results. In this manner, economical time counters may be used in the analyzer while still permitting relatively accurate absolute times to be assigned to the test results. Thus, errors caused by adjusting the time counter, as well the additional cost of unnecessary operational elements of the analyzer, are eliminated.

In accordance with the present invention, conventional quartz clocks or electronic shift registers may be used as the time counter in the analyzer. It is immaterial in the present invention whether the time counter delivers actual clock time or merely the count status of a shift register. However, it is important that the time counter be free of unduly large inaccuracies. Therefore, the time counter's rate should be as constant as possible, and known beforehand, to allow differences from various counts to be accurately converted into time differences or absolute times. Such calculations can be made using the following formula:

$$t_A = t_D - (n_D - n_A)/v$$

where $t_A$ is the absolute time at which a test A was carried out;

$t_D$ is the time of data transfer, that is a time at which the time value of the time counter can be compared with the clock time of the time standard, $n_D$ is the count of the time counter at time $t_D$, $n_A$ is the count of the time counter that was stored at the time of testing, and v is the time counter's rate, for instance in minutes per counter unit.

Preferably, the rate v is known beforehand and the DPU is programmed to take the rate into account. Alternatively, the rate v may be transferred from the analyzer to the DPU. In yet another embodiment, the rate can be ascertained by the DPU by performing two or more data transfers at separate points in time and calculating v as follows:

$$v = (n_2 - n_1)/(t_2 - t_1).$$

The difference between two time counter values, $n_2 - n_1$, is divided by the associated difference between the time standard's times. As used herein, "associated" denotes that $t_1$ and $n_1$ as well as $t_2$ and $n_2$ are ascertained at the same real time. The more time between the times $t_1$ and $t_2$, the more accurate the determination of the rate v. In addition, rate determinations can be carried out by storing the (t,n) values of one or more previous data transfers and determining v whenever a new data transfer is performed, taking into account the stored values as well as the current value of the set (t,n). The present invention provides independence from offset, that is independence from adjustment of the time counter when absolute times are ascertained for tests. Preferably, the time counter starts when applying an operational power source. An embodiment is envisioned wherein the user may set the time counter. However, the user is preferably precluded from affecting the time counter's time values. A preferred embodiment is described in relation to FIG. 2.

In the sense of the present invention, analyzers are not only blood sugar testers, but testers in general that are suitable to record a number of test results in order to ascertain from them a time function of an analyte. Therefore, the present invention also applies to measuring coagulation factors and ecological parameters such as nitrite, sulfur dioxide, ozone and the like. Although when monitoring the time function of analytes it is often advantageous to have a plurality of data records containing test results and relative time values, the present invention is also applicable if the analyzer only stores one set of data. An analyzer in accordance with the present invention has a memory to store one or more data records. As a rule, commercial blood sugar testers are already equipped with such a memory. Moreover, the analyzer also comprises a device to transfer stored data records to the DPU. In commercially available systems, data transfer is implemented using cables and plug-in connections. Additionally, data transfers may be implemented by optical coupling in the manner described for instance in the European patent document EP-A 0,636,878. A very simple and user friendly data transfer approach consists of fitting the analyzer with a transmitter for wirelessly transferring the data to the DPU in the absence of a mechanical coupling. This feature can be implemented by an infrared diode in the analyzer and a corresponding infrared detector in the DPU. Similar transmission systems are currently used in TV remote controls. In such a case, the data transfer is accomplished by means of modulated light. Preferably, the data transfer will not be a solely unidirectional transfer from the analyzer to the DPU. Ideally, the DPU also contains a unit to transmit data to the analyzer thereby allowing for bidirectional communications between the analyzer and the DPU. This feature offers an advantageous application in that the DPU may call the analyzer and request data. Additionally, upon data transmission, the DPU may acknowledge receipt, thereby ensuring that the data exchange has been carried out in full.

A preferred DPU for processing test results can be in the form of a personal computer with appropriate software. However, the DPU also may be a convenient unit such as a notebook, notepad, palmtop or the like. Preferably, the DPU contains an arithmetic logic unit (ALU), a memory unit and a test result display.

The processing of the test results by the DPU may include calculations to convert the test results into other units or to determine analyte concentrations from the test results. The processing of the test results may also be used to obtain graphics, trends and correlation of parameters and changes in test results. Illustratively, the test result processing may be carried out in such a manner that the diabetic learns from it how to behave and which insulin doses must be injected to attain a blood sugar level which is as uniform as possible and within the standard range. The DPU is fitted with a device to receive data records from the analyzer. As already described in relation to the analyzer, such a device may be implemented by electrical feeds or also by radio or optical receivers.

The DPU contains a time-standard used as a reference in converting the time values of the analyzer into absolute time values. Accordingly, time values in the sense of the invention need not be inherently true ones, the concept being understood in the sense that contrary to the time counter time value, which may be a number or a completely artificial clock time, the conversion is carried out to a clock time (and date) which are corrected for offsets and where applicable for clock inaccuracies. Suitable time standards for instance are quartz clocks of high accuracy and radiowave controlled clocks. While the quartz clocks typically contained in computers do not offer particularly high accuracy, they may be simply set and reset by the user. For several reasons, setting the time standard in the computer is less a drawback than setting the clock contained in the analyzer. As an example, the time standard on the computer can be set simply and conveniently using a keyboard. If necessary, the DPU can be placed under the control of a treating physician or other appropriate professional, thereby precluding manipulation. If every owner of an analyzer does not have access to their own DPU, the analyzer owners may rely on their physician or professional having such a DPU. Therefore, one DPU may be used to process data from many different analyzers. Hence, only one time standard is needed and has to be controlled to monitor a plurality of analyzers.

The present invention further relates to a method for evaluating test results using a system composed of an analyzer and a DPU. In accordance with the method, testing is implemented with the analyzer and one or more data records containing test results and relative time values ascertained by an integrated time counter at the time of the particular tests are stored. The data records and the instantaneous time counter time values are then transferred to the DPU. The times at which the tests were carried out are computed from the relative test time values by comparing the instantaneous time value with the absolute time value of a time standard in the DPU.

Operation of a preferred method of the present invention can be better explained by the following example. When a power source is connected to the time counter, the time counter begins to run at a constant and known rate. The user carries out a first measurement at time T1. Some time later, the user goes to his physician where the test results are transferred to the DPU at time T2. The instantaneous time value of the time counter is transferred together with the test results and the associated time value. The DPU calculates the difference between the time counter's instantaneous value and the associated relative time value of the time standard. The relative time values of the data records are calculated by subtracting the associated time values from the time value of a subsequent evaluation of the test results. It will be appreciated that the time values of the time counter and the time standard used in calculating the difference must represent the same real time. Therefore, the instantaneous time counter time value is preferably transferred to form the difference and the time value of the time standard at the time of transfer is used to calculate the absolute time.

The invention offers another advantage in that the data transfer may be used to affect synchronization between the analyzer and the DPU. The time-counter may be set or the status of the time counter and the associated time standard time may be stored such that this data may be used as a new basis of calculation to convert the time values into absolute times. As a result, time counter offsets and clock inaccuracies occurring before synchronization no longer affect time computations made after synchronization.

The Table below clearly shows the advantages of a system of the invention.

This Table is based on a time counter which is inaccurate in that it runs slow by about 10 sec/day. Row 2 of the Table shows that an inaccuracy of 5 minutes arises for a measurement taken one month after setting the time counter. If the patient calls on his physician 2 days later and the test values are transferred, the system of the invention recognizes that a time difference between the time counter and the time standard of 5 min

TABLE 1

|  | time-counter | time-standard | row |
|---|---|---|---|
| factory set | 15 June 97 9:30:00 am | 15 June 97 9:30:00 am | 1 |
| test I | 15 July 97 8:40:00 am | 15 July 97 8:45:00 am | 2 |
| transfer | 17 July 97 10:25:00 am | 17 July 97 10:30:20 am | 3 |
| transfer | 15 June 2002 9:30:00 am | 15 June 2002 2:30:00 pm | 4 |
| test II | 16 June 2002 9:30:00 am | 16 June 2002 2:30:10 pm | 5 |
| transfer | 22 June 2002 10:00:00 am | 22 June 2002 3:01:10 pm | 6 |

20 sec has arisen. By merely adding this difference to the time value of test I, the system reduces the operational difference of 5 minutes to one of 20 seconds. When using the analytical system to check the progress of blood-sugar levels, an operational difference of 5 minutes is trivial. For that reason, Table 1 shows a corresponding case for a measurement 5 years after setting the time counter. Row 4 of Table 1 shows that an operational difference of 5 hours is already present when a test is taken on Jun. 15, 2002. If the test results in 2002 were evaluated without a correction, then a progress check for the blood-sugar level would be wholly defective because a blood sugar level at lunch time would be interpreted as a morning blood sugar level. A measurement as shown in row 5 of Table 1 is easily corrected if at the next transfer of test values the time difference between time counter and time standard is ascertained and used for correction. For example, if a transfer is carried out on Jun. 22, 2002, the time difference is calculated as being 5 hours 1 minute and 10 seconds. By adding this difference to the value of the time counter as of Jun. 16, 2002 (column 5), the inaccuracy can be reduced to 1 minute, said latter value being well within acceptable ranges for ordinary progress checks. Advantageously, the time value ascertained from the time counter can be corrected for tests run at a given time by interpolating clock inaccuracies that were determined at the transfer before the test and after the test. The data shown in rows 4 and 6 illustratively indicate that a clock inaccuracy of 70 seconds arose within 7 days. Accordingly, the conclusion can be drawn that an additional 10 seconds of clock inaccuracy were added to the clock inaccuracy ascertained by difference formation on Jun. 15, 2002 in the time interval to the test (row 5). However, because in practice clock inaccuracies tend not to be material constants but are caused by temperature and other factors, the accuracy made possible by interpolation is limited.

The methods of the present invention can be improved by transferring one or more check sums together with the data records to the DPU so that the data records can be monitored to determine whether or not the data transfer was error free. In addition, it is advantageous to simultaneously transfer an instrument specific marker of the particular analyzer to allow the DPU to distinguish between different analyzers. As mentioned above, the present invention comprehends that a number of users will come to the physician or professional with their own analyzers to secure a DPU evaluation. Mistaken identity problems may be precluded by using particular markers to identify the particular analyzers.

DETAILED DESCRIPTION OF THE PREFERRED EMBODIMENTS

Figure 1:
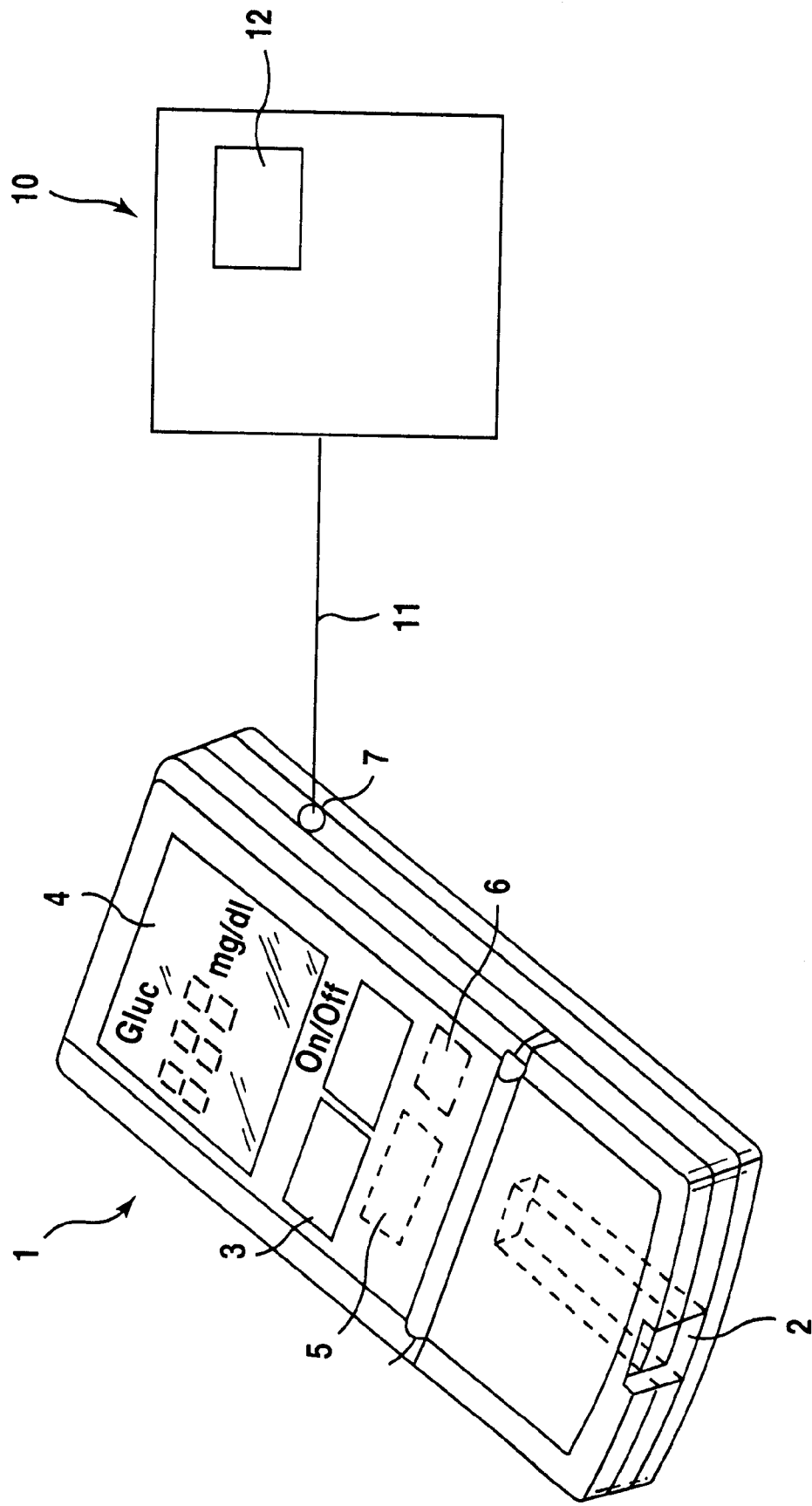
FIG. 1 shows an analyzer in accordance with the present invention.

FIG. 1 shows an analyzer 1 operating by means of test elements inserted into a cavity 2 in the analyzer. This analyzer is fitted with operational actuators 3 and a display 4 to display the test results. A memory 5 integrated into the analyzer 1 is especially important in the present invention because it allows the analyzer to store data records containing test results and associated time values. The analyzer further comprises a time counter for transmitting time values to the memory 5. The analyzer is also fitted with a jack 7 for receiving a cable terminal 11 of the DPU 10 in order to communicate with said DPU. In addition, the DPU also contains an ALU and the time standard 12.

Figure 2:
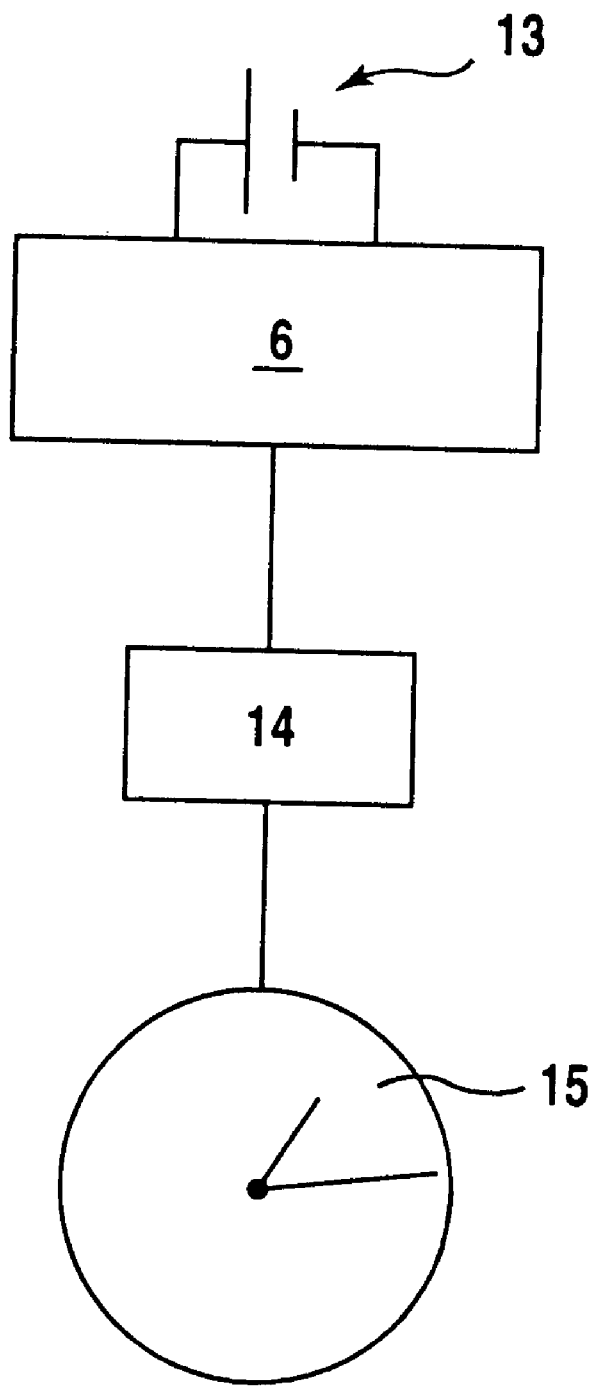
FIG. 2 shows a time-counter that is activated by being connected to a power source.

FIG. 2 shows a time counter 6 which is started upon being connected to the battery 13. The status of the time counter is transferred to a converter 14 which ascertains from the status a clock time shown on the display 15. The user is able to reprogram the converter 14 by using keys, in other words, he can set the clock. However, the time counter value is unaffected by this customer intervention and clock adjustment does not cause an error in calculating the absolute times at which the tests were run. If the user takes measurements through the winter and then sets the clock to summer time, the time counter will remain unaffected and unambiguous assignment of the measurements to absolute times remains possible.

I claim:

1. An analyzing system comprising:
   an analyzer that performs tests to generate test results in the form of data records, wherein the analyzer includes an integrated time counter for generating time counter time values, a memory for storing the data records from the test results and the time counter time values and a transferring device for transferring the data records and the time counter time values; and
   a data processing unit for processing the stored data records, wherein the data processing unit includes a receiving device for receiving the data records and the time counter time values from the transferring device, a time standard for producing a time standard time value, and an arithmetic logic unit for converting the time counter time values into absolute time values on the basis of a comparison of the time counter time values with the time standard time value.

2. The analyzing system of claim 1, wherein the data transfer is carried out using a modulated light source as the transferring device in the analyzer and a light-sensitive detector as the receiving device in the data processing unit.

3. The analyzing system of claim 1, wherein the analyzer performs tests on body fluids.

4. The analyzing system of claim 3, wherein the body fluid is blood and the analyzer is a blood sugar level tester.

5. The analyzing system of claim 1, wherein the analyzer is fitted with a converter for converting the time counter time values into clock time values.

6. The analyzing system of claim 5, wherein the converter is programmable by a user and/or the data processing unit to correct the clock time.

7. A method of evaluating test results from a system including an analyzer and a data processing unit, comprising the steps of:
performing a test with the analyzer to produce test results;
producing a test time value with an integrated time counter when the test is performed;
storing the test results and the test time value in a data record;
transferring the data record containing the test results and the test time value to the data processing unit,
producing an instantaneous time value with the integrated time counter at the time at which the data record is transferred and transferring the instantaneous time value to the data processing unit;
computing the actual time value at which the test was carried out from the test time value by comparing the instantaneous time value with the accurate time value of a time standard in the DPU,
evaluating the test data on the basis of the calculated actual time value.

8. The method of claim 7, wherein the transferring step is accomplished by transmitting a modulated light from the analyzer and receiving the modulated light with a light detector in the data processing unit.

9. The method of claim 7, wherein a time difference is obtained from the time value of the time standard at a given time and the time value of the time counter at the same given time and the time value of the data record is converted into an absolute time value by adding the time difference to the time value of the data record.

10. The method of claim 9, wherein a first time difference between the time standard time value and the time counter time value is determined during a first data transfer and a second time difference between the time standard time value and the time counter time value is determined during an ensuing second data transfer and the absolute time values between the data transfers are determined by interpolation between the first and second time difference and addition of the interpolated time difference to the test time value.

11. The method of claim 7 further comprising the step of transferring one or more check sums with the data record to the data processing unit.

12. The method of claim 7 further comprising the step of transferring an analyzer marker to the data processing unit.

13. The method of claim 7 further comprising the step of the transmitting a request for a data transfer from the data processing unit to the analyzer and acknowledging the data record was received by the data processing unit.

14. The method of claim 7, wherein the time counter counts at a predetermined rate (v) and the calculation of the actual testing time ($t_A$) is based on the formula $$t_A = t_D - (n_D - n_A)/v$$

where $t_D$ is the time value of the time standard at the time of data transfer, $n_D$ is the time value of the time counter at the time of data transfer, $n_A$ is the time value of the time counter stored at the time of testing, and v is the rate of the time counter.

15. The method of claim 7 further comprising the steps of using a converter to convert the time value of the time counter into clock time and reprogramming the converter to correct the clock time.

16. An analyzing system comprising:
analyzing means for performing tests and generating test results in the form of data records wherein the analyzing means further include;
time counter means for generating time counter time values,
memory means for storing the data records from the test results and the time counter time values, and
transferring means for transferring the data records and the time counter time values; and
data processing means for processing the stored data records wherein the data processing means further include;
receiving means for receiving the data records and the time counter time values from the transferring means,
time standard means for producing a time standard time value, and
arithmetic logic means for converting the time counter time values into absolute time values on the basis of a comparison of the time counter time values with the time standard time value.

17. The analyzing system of claim 16, wherein the analyzing means are for testing body fluids.

18. The analyzing system of claim 16, wherein the analyzing means are for testing blood sugar levels.

19. The analyzing system of claim 16, wherein the analyzing means further comprise converter means for converting the time counter time values into clock time values.

20. The analyzing system of claim 19, wherein the converter means are programmable by a user and/or the data processing means to correct the clock time.

21. An analyzer system for performing tests to generate test results in the form of data records comprising:
an analyzer that includes an integrated time counter means for generating time stamps which indicate the date and time when said tests were performed, a memory means for storing said data records and said time stamps, and a transferring means for transferring the data records and the time stamps; and
a data processing means for processing the stored data records, wherein said data processing means includes a receiving means for receiving the data records and time stamps from the transferring means, a time standard means for producing an absolute reference time, and an arithmetic logic means for converting the time stamps into absolute reference time values on the basis of a comparison of the time stamps with the absolute reference time.

* * * * *